(12) United States Patent
Hk

(10) Patent No.: US 9,022,033 B2
(45) Date of Patent: May 5, 2015

(54) ADAPTABLE OXYGEN REGULATOR SYSTEM AND METHOD WITH AN ELECTRONIC CONTROL DEVICE

(75) Inventor: Anurag Sharma Hk, Bangalore (IN)

(73) Assignee: Airbus Engineering Centre India, Bangalore, Karnataka (IN)

( * ) Notice: Subject to any disclaimer, the term of this patent is extended or adjusted under 35 U.S.C. 154(b) by 509 days.

(21) Appl. No.: 13/390,517

(22) PCT Filed: Aug. 19, 2010

(86) PCT No.: PCT/IN2010/000550
§ 371 (c)(1),
(2), (4) Date: Feb. 14, 2012

(87) PCT Pub. No.: WO2011/033525
PCT Pub. Date: Mar. 24, 2011

(65) Prior Publication Data
US 2012/0160244 A1 Jun. 28, 2012

(30) Foreign Application Priority Data

Sep. 16, 2009 (IN) .......................... 2255/CHE/2009

(51) Int. Cl.
*A61B 5/1455* (2006.01)
*B64D 10/00* (2006.01)
(Continued)

(52) U.S. Cl.
CPC .......... *B64D 10/00* (2013.01); *A61M 16/0051* (2013.01); *A61M 16/12* (2013.01);
(Continued)

(58) Field of Classification Search
CPC .......... A61M 16/0051; A61M 16/06; A61M 16/0677; A61M 16/10; A61M 16/00; A61M 11/00; A61M 16/207; A61M 16/20; A61M 16/12; A61M 16/125; A62B 7/14; A62B 9/006; A62B 9/02; A62B 9/022; A62B 9/027; A62B 9/00; A62B 7/00; B64D 11/00; B64D 11/06; B64D 13/04; B64D 13/06; B64D 10/00; B64D 13/00; B64D 37/00; B64D 37/32; B64D 13/02; G01L 19/04; G05D 16/2013; F16K 31/02; H03M 1/48; A61B 5/00; A61B 5/14551; A61B 5/417
USPC ............ 128/200.24, 202.12, 202.22, 204.21, 128/204.22, 204.23, 204.29, 205.11, 128/205.23, 204.26, 202.26, 205.24, 128/204.18, 201.25, 201.28, 202.11, 128/205.25, 204.25, 204.24; 244/118.5; 600/310, 323, 532, 19; 700/282; 137/81.1, 122, 505.28, 38; 62/402, 62/271, 655, 172, 401, 78, 86; 454/72; 341/115, 116; 701/10
See application file for complete search history.

(56) References Cited

U.S. PATENT DOCUMENTS 3,526,239 A 9/1970 Oroza
3,675,649 A 7/1972 Basham et al.
(Continued)

FOREIGN PATENT DOCUMENTS

WO 2008010015 A1 1/2008

OTHER PUBLICATIONS

Supplementary European Search Report—EP Application No. 10816804.8—European Patent Office, Munich—Mar. 13, 2013.
(Continued)

*Primary Examiner* — Annette Dixon
(74) *Attorney, Agent, or Firm* — Prakash Nama; Global IP Services, PLLC

(57) ABSTRACT

A system and method for an adaptable oxygen regulator with an electronic control device is disclosed. In one embodiment, an oxygen regulator system includes an electronic control device which includes a non-volatile memory for storing a first reference point. The electronic control device also includes a pressure sensor configured for generating pressure data of the pressurized aircraft cabin. The electronic control device further includes a logical control unit for generating a control signal by processing the first reference point and the pressure data. Further, the electronic control unit includes a rotary actuator for generating a rotary displacement based on the control signal. Moreover, the oxygen regulator system includes a demand dilution oxygen regulator coupled to the electronic control unit and configured to control the supply of oxygen and the flow of dilution air from the pressurized aircraft cabin based on the control signal.

20 Claims, 6 Drawing Sheets

(51) Int. Cl.
*A61M 16/00* (2006.01)
*A61M 16/12* (2006.01)
*A61M 16/20* (2006.01)
*A62B 7/14* (2006.01)
*A62B 9/00* (2006.01)

(52) U.S. Cl.
CPC ...... *A61M 16/20* (2013.01); *A61M 2202/0208* (2013.01); *A61M 2205/3358* (2013.01); *A61M 2230/205* (2013.01); *A62B 7/14* (2013.01); *A62B 9/006* (2013.01); *B64D 2231/02* (2013.01); *A61M 16/125* (2013.01); *A61M 16/207* (2013.01)

(56) References Cited

U.S. PATENT DOCUMENTS

| | | | |
|---|---|---|---|
| 4,336,590 A * | 6/1982 | Jacq et al. | 128/204.21 |
| 4,648,397 A | 3/1987 | Beale | |
| 6,244,540 B1 | 6/2001 | Stabile et al. | |
| 2004/0206353 A1 | 10/2004 | Conroy, Jr. | |
| 2007/0144597 A1 | 6/2007 | Cazenave et al. | |
| 2008/0053541 A1 | 3/2008 | Meckes et al. | |

OTHER PUBLICATIONS

UK Search Report—GB Application No. 0919818.5—UKIPO—Feb. 23, 2010.

* cited by examiner

ADAPTABLE OXYGEN REGULATOR SYSTEM AND METHOD WITH AN ELECTRONIC CONTROL DEVICE

FIELD OF TECHNOLOGY

The present invention relates to the field of aeronautical and/or aeromedical engineering. In particular, the present invention relates to oxygen regulator systems and methods.

BACKGROUND

Typically in an aircraft, aircraft cabin air pressure in terms of pressure altitude is in the range of 3000 to 8000 feet, which is generally less than a pressure encountered at a ground level. Persons with impaired pulmonary capacity are not fit to travel in the reduced aircraft cabin air pressure associated with low oxygen levels (e.g., due to recirculation of aircraft cabin air by air conditioning/environmental control system (ECS) in the aircraft). This is especially true for persons suffering or predisposed to conditions including but not limited to chronic bronchitis, emphysema, bronchiectasis, dyspnoea at rest, corpulmonale, severe asthma, anemia (sickle cell hemoglobin and beta-thalassaemia) and the like. This can also include persons who have undergone recent lung, chest injury/surgery/pulmonary infections. That is, the persons to whom exposure to higher altitudes/low oxygen levels normally encountered in an aircraft cabin may cause under oxygenation of blood hemoglobin and subsequent tissue hypoxia.

Currently, such individuals are transported using a flight that provides special oxygen supply and cabin altitude not exceeding a guaranteed 3500/4000 feet ambient. This may require flying at an extraordinarily uneconomical altitude for the aircraft or evacuating using dedicated military aircraft (such as turboprop or chartered flights) with large volume oxygen supply on board. In either case, it is a high cost that is generally not covered by social health schemes and health insurances. For short distances, helicopters are used typically for such purposes.

However, none of these current solutions may be economically viable as they all require flying at nearly surface level, monitoring and adjusting oxygen by medical attendants, remaining on a large volume oxygen supply, and so on. Further, today's oxygen regulators for aviation use operate above a pressure altitude of 10000 to 12000 feet.

SUMMARY

Adaptable Oxygen regulator system and method with an electronic control device is disclosed. According to an aspect of the present invention, an electronic control device for an oxygen regulator operable inside a pressurized aircraft cabin to supply an appropriate rate of oxygen to a breathing apparatus of a subject in the pressurized aircraft cabin includes a non-volatile memory. The non-volatile memory is configured for storing a first reference point for increasing a supply of oxygen from an oxygen bottle coupled to the oxygen regulator to the breathing apparatus and for stopping a flow of dilution air from the pressurized aircraft cabin to the breathing apparatus at a preconfigured pressure altitude (e.g., 2000 feet) above the first reference point. The electronic control device also includes a pressure sensor configured for generating pressure data of the pressurized aircraft cabin.

Further, the electronic control device includes a logical control unit coupled to the non-volatile memory and the pressure sensor. The logical control unit is configured for generating a control signal to regulate the supply of oxygen from the oxygen bottle and the flow of dilution air from the pressurized aircraft cabin via the oxygen regulator to the breathing apparatus by processing the first reference point and the pressure data. Furthermore, the electronic control device includes a serial port coupled to the logical control unit for receiving oxyhaemoglobin saturation data forwarded by a pulse oximeter worn by the subject. In addition, the electronic control device includes an amplifier coupled to the logical control unit for amplifying the control signal. Moreover, the electronic control device includes a rotary actuator coupled to the amplifier for performing the rotary displacement based on the control signal.

According to another aspect of the present invention, an oxygen regulator system operable inside a pressurized aircraft cabin to supply an appropriate rate of oxygen to a breathing apparatus of a subject in the pressurized aircraft cabin includes an electronic control unit and an oxygen regulator coupled to the electronic control unit. The electronic control unit includes a non-volatile memory configured for storing a first reference point for start increasing a supply of oxygen from an oxygen bottle coupled to the oxygen regulator to the breathing apparatus and for stopping a flow of dilution air from the pressurized aircraft cabin to the breathing apparatus at a preconfigured pressure altitude (e.g., 2000 feet) above the first reference point. The electronic control unit also includes a pressure sensor configured for measuring pressure in the pressurized aircraft cabin.

Further, the electronic control unit includes a logical control unit coupled to the non-volatile memory and the pressure sensor. The logical control unit is configured for generating a control signal to regulate the supply of oxygen from the oxygen bottle and the flow of dilution air from the pressurized aircraft cabin via the oxygen regulator to the breathing apparatus by processing the first reference point and the pressure data. In addition, the electronic control unit includes a rotary actuator coupled to the logical control unit for generating a rotary displacement based on the control signal.

The oxygen regulator coupled to the electronic control unit is configured to control the supply of oxygen and the flow of dilution air from the pressurized aircraft cabin based on the control signal. The oxygen regulator system also includes a pulse oximeter worn by the subject and coupled to the electronic control unit.

According to yet another aspect of the present invention, a method of an electronic control device for an oxygen regulator operable inside a pressurized aircraft cabin to supply an appropriate rate of oxygen to a breathing apparatus of a subject in the pressurized aircraft cabin includes storing a first reference point. The first reference point is for start increasing a supply of oxygen from an oxygen bottle coupled to the oxygen regulator to the breathing apparatus and for stopping a flow of dilution air from the pressurized aircraft cabin to the breathing apparatus at a preconfigured pressure altitude (e.g., 2000 feet) above the first reference point.

The method also includes generating pressure data of the pressurized aircraft cabin using a pressure sensor of the electronic control device. The method further includes generating a control signal using a logical control unit coupled to the non-volatile memory and the pressure sensor to regulate the supply of oxygen and the flow of dilution air from the pressurized aircraft cabin via the oxygen regulator to the breathing apparatus by processing the first reference point and the pressure data.

The methods, apparatuses and systems disclosed herein may be implemented in any means for achieving various aspects. Other features will be apparent from the accompanying drawings and from the detailed description that follow.

BRIEF DESCRIPTION OF THE DRAWINGS

Various preferred embodiments are described herein with reference to the drawings, wherein.

The drawings described herein are for illustration purposes only and are not intended to limit the scope of the present disclosure in any way.

DETAILED DESCRIPTION

Adaptable oxygen regulator system and method with an electronic control device is disclosed. In the following detailed description of the embodiments of the invention, reference is made to the accompanying drawings that form a part hereof, and in which are shown by way of illustration specific embodiments in which the invention may be practiced. These embodiments are described in sufficient detail to enable those skilled in the art to practice the invention, and it is to be understood that other embodiments may be utilized and that changes may be made without departing from the scope of the present invention. The following detailed description is, therefore, not to be taken in a limiting sense, and the scope of the present invention is defined only by the appended claims.

The terms 'oxygen bottle' and 'personal portable oxygen bottle' are interchangeably used throughout the document. Also, the terms 'oxygen' and 'pressurized oxygen' are interchangeably used throughout the document. Further, the terms 'air' and 'aircraft cabin air' are interchangeably used throughout the document. The terms 'altitude' and 'aircraft cabin pressure altitude' are used interchangeably throughout the document.

Figure 1:
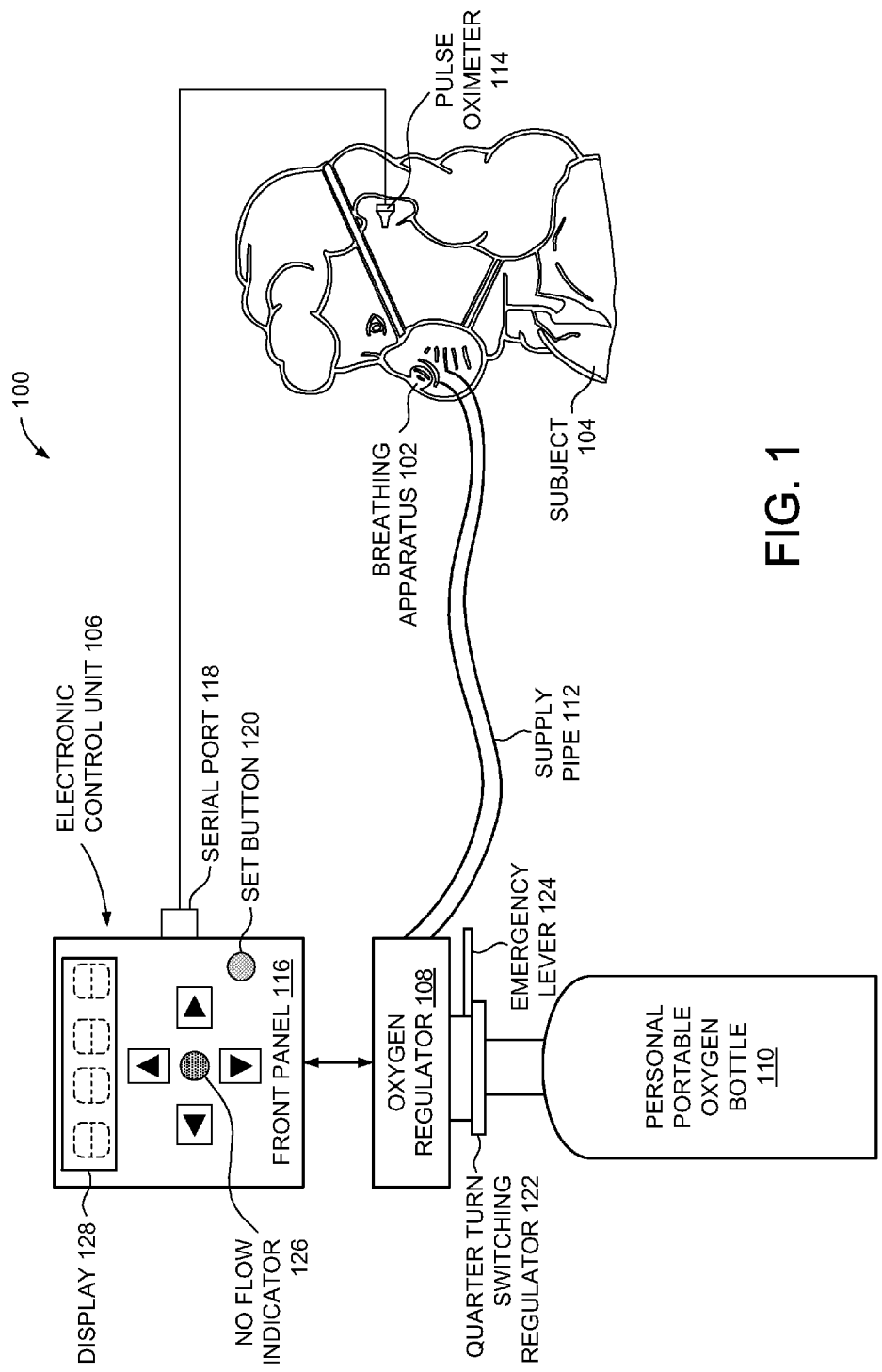
FIG. 1 illustrates an exemplary oxygen regulator system, according to an embodiment of the invention.

FIG. 1 illustrates an exemplary oxygen regulator system 100, according to an embodiment of the invention. The oxygen regulator system 100, which is carried by a subject 104, is currently placed in a pressurized aircraft cabin that boards the subject 104. The subject 104 may be a passenger or cabin crew predisposed to a pulmonary disorder, and is hence shown wearing a breathing apparatus 102 in the pressurized aircraft cabin.

As shown in FIG. 1, the oxygen regulator system 100 includes an oxygen regulator 108 with an electronic control unit 106 and a personal portable oxygen bottle 110. The oxygen regulator 108 with the electronic control unit 106 is screwed on top of the personal portable oxygen bottle 110. The personal portable oxygen bottle 110 has a capacity of approximately 2 to 7 liters. It can be also seen in FIG. 1 that, the oxygen regulator 108 is coupled to the breathing apparatus 102 of the subject 104 via a supply pipe 112 to supply an appropriate rate of the pressurized oxygen to the subject 104.

The electronic control unit 106 includes a front panel 116. The front panel 116 includes a set button 120, a no flow indicator 126 and a display 128. In an example operation of the oxygen regulator system 100, a first reference point is entered by a physician of the subject 104 using the set button 120 for setting the pressure altitude at which the oxygen regulator 108 starts regulating flow of the pressurized oxygen to the breathing apparatus 102. The first reference point is displayed in the display 128, and is configured to increase a supply of the pressurized oxygen to the breathing apparatus 102 and to stop flow of dilution air from the pressurized aircraft cabin to the breathing apparatus 102 at a preconfigured pressure altitude (e.g., 2000 ft) above the first reference point, as will be illustrated in more details in FIG. 2. The display 128 also displays an aircraft cabin pressure altitude during this setting procedure and the breathing rate during operation of the system.

The no flow indicator 126 indicates a no flow condition of the pressurized oxygen to the breathing apparatus 102 when the oxygen regulator system 100 fails or when the personal portable oxygen bottle 110 becomes empty. The electronic control unit 106 also includes a serial port 118 for receiving oxyhaemoglobin saturation data forwarded by a pulse oximeter 114 worn by the subject 104. In one embodiment, the oxygen regulator 108 regulates supply of oxygen to the breathing apparatus 102 based on the oxyhaemoglobin saturation data.

In an exemplary operation, a physician or a responsible caretaker of the subject 104, who is expected to fly in the pressurized aircraft cabin, enters the first reference point based on a prior lung capacity test of the subject 104 (e.g., using the set button 120). Further, the second reference point is automatically set based on the first reference point. Then, the flow of pressurized oxygen is initiated from the personal portable oxygen bottle 110 using a quarter turn switching regulator 122. The oxygen regulator 108 increases supply of oxygen to the breathing apparatus 102 based on the first reference point.

Further, the oxygen regulator 108 gradually increases supply of oxygen (by gradually stopping aircraft cabin dilution airflow) with increasing aircraft cabin pressure altitude to output approximately about 100% pressurized oxygen into the breathing apparatus 102 upon reaching the second reference point. The oxygen regulator system 100 also includes an emergency lever 124 or emergency dilution shutoff lever operable for supplying pressurized oxygen at a maximum level (e.g., approximately about 100%), if the subject 104 desires to at any time (e.g., based on the condition of the subject 104 and irrespective of aircraft cabin pressure altitude).

Figure 2:
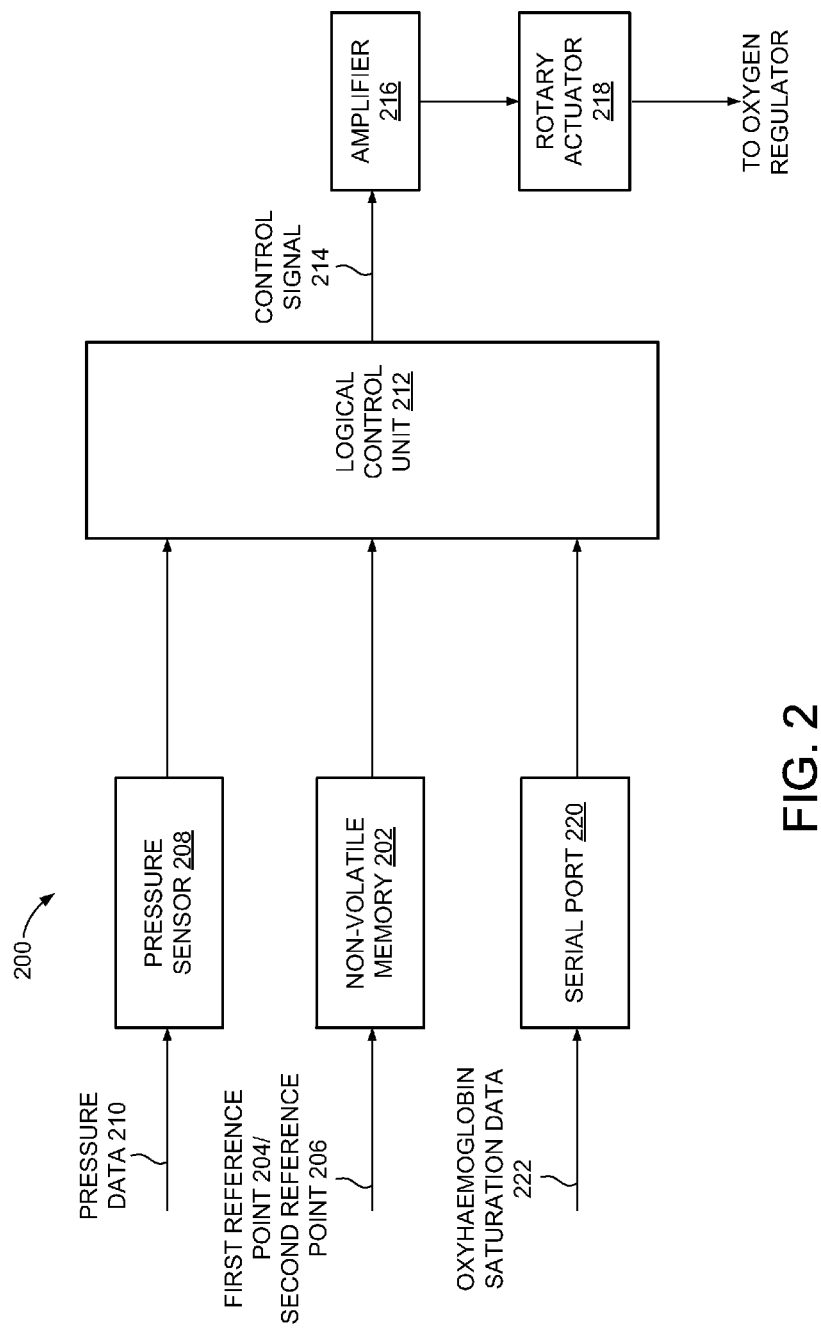
FIG. 2 illustrates an exemplary electronic control device for the oxygen regulator of FIG. 1, according to an embodiment of the invention.

FIG. 2 illustrates an exemplary electronic control device 200 for the oxygen regulator 108 of FIG. 1, according to an embodiment of the invention. The electronic control device 200 can be used with the oxygen regulator 108 that is operable inside a pressurized aircraft cabin to supply an appropriate rate of oxygen to the breathing apparatus 102 of the subject 104 in the pressurized aircraft cabin. It is appreciated that, the electronic control device 200 is an exemplary embodiment of the electronic control unit 106 of FIG. 1.

As shown in FIG. 2, the electronic control device 200 includes a non-volatile memory 202, a pressure sensor 208, a logical control unit 212, an amplifier 216, a rotary actuator 218 and a serial port 220. The logical control unit 212 is coupled to the non-volatile memory 202, the pressure sensor 208 and the serial port 220. The amplifier 216 is coupled to the logical control unit 212 and the rotary actuator 218 is coupled to the amplifier 216. The non-volatile memory 202 may be a flash memory. In one embodiment, the non-volatile memory 202 is configured for storing a first reference point 204. The first reference point 204 is operable for increasing a supply of oxygen from a personal portable oxygen bottle 110 coupled to the oxygen regulator 108 to the breathing apparatus 102. A second reference point 206 may be automatically set at a preconfigured pressure altitude (e.g., 2000 ft) above the first reference point and is operable for stopping a flow of dilution air from the pressurized aircraft cabin to the breathing apparatus 102.

The pressure sensor 208 is used to measure air pressure of the pressurized aircraft cabin boarding the subject 104. In an exemplary operation, the logical control unit 212 generates a control signal 214 by processing the first reference point 204 and pressure data 210 from the pressure sensor 208. In one embodiment, the control signal 214 is operable for regulating the supply of oxygen from the personal portable oxygen bottle 110 and the flow of dilution air from the pressurized aircraft cabin via the oxygen regulator 108 to the breathing apparatus 102, as will be described in greater detail in FIG. 4. The amplifier 216 amplifies the control signal 214 and forwards the control signal 214 to the rotary actuator 218.

The rotary actuator 218 performs a rotary displacement based on the control signal 214, thus enabling the oxygen regulator 108 to supply an appropriate rate of oxygen to the breathing apparatus 102. Additionally, the serial port 220 of the electronic control device 200 receives oxyhaemoglobin saturation data 222 forwarded by the pulse oximeter 114. In one example embodiment, when the oxyhaemoglobin saturation data 222 is less than a threshold value, the logical control unit 212 generates the control signal 214 such that the oxygen regulator 108 increases supply of oxygen to a maximum level.

Figure 3:
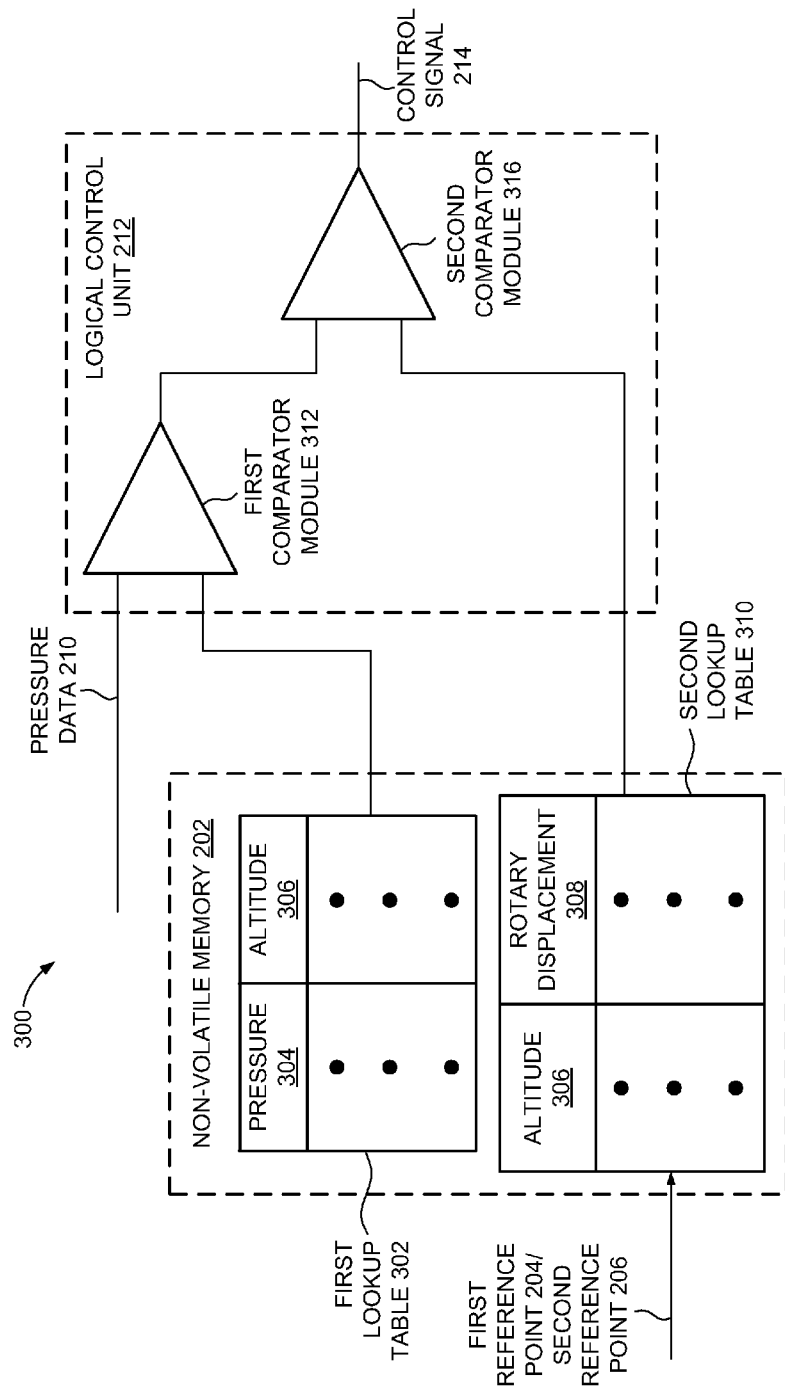
FIG. 3 illustrates an exploded view of the non-volatile memory and the logical control unit of FIG. 2, according to an embodiment of the invention.

FIG. 3 illustrates an exploded view 300 of the non-volatile memory 202 and the logical control unit 212 of FIG. 2, according to an embodiment of the invention. As shown in FIG. 3, the non-volatile memory 202 includes a first lookup table 302 and a second lookup table 310. The first lookup table 302 includes a pressure data column 304 including pressure data and an altitude column 306 including altitude values corresponding to the pressure data. The second lookup table 310 includes the altitude column 306 including the corresponding altitude values and a rotary displacement column 308 including rotary displacement values corresponding to the altitude values. Further, the logical control unit 212 includes a first comparator module 312 and a second comparator module 316 coupled to the first comparator module 312.

In an exemplary operation, the first comparator module 312 compares the pressure data 210 with the pressure data in the first lookup table 302 and determines corresponding altitude using the first lookup table 302. In one exemplary implementation, the first lookup table 302 is used to convert the pressure data to the corresponding altitude. The output of the first comparator module 312 is fed as an input to the second comparator module 316.

The second comparator module 316 compares the corresponding altitude with the corresponding altitude values in the second lookup table 310, determines a corresponding rotary displacement, and generates the control signal 214 based on the rotary displacement. The rotary displacement is obtained from the second lookup table 310 used to convert the corresponding altitude to the rotary displacement. Also, the rotary displacement is determined based on the first reference point 204 and the second reference point 206. As described above, the control signal 214 is used to perform a rotary displacement for regulating the supply of oxygen from the oxygen regulator 108, as described in greater detail below.

Figure 4:
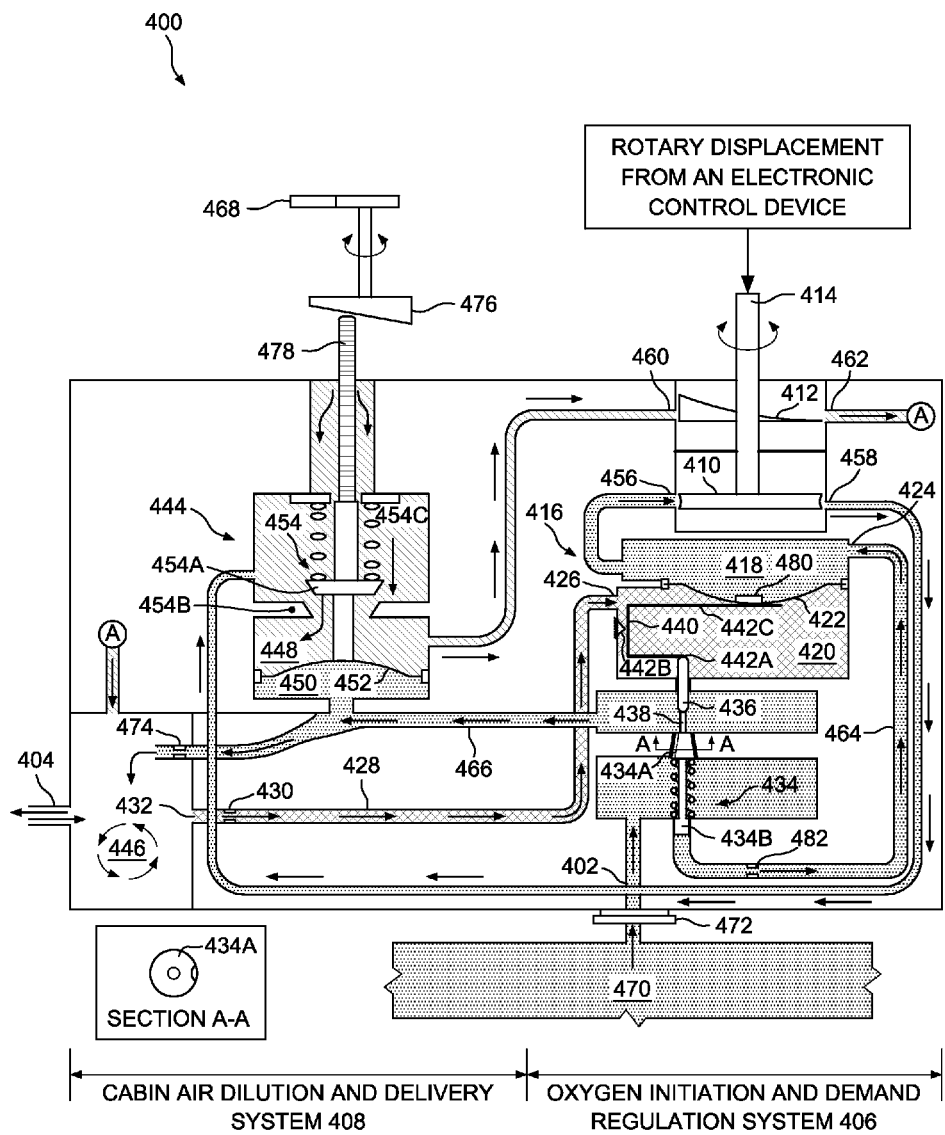
FIG. 4 illustrates an exemplary oxygen regulator, according to an embodiment of the invention.

FIG. 4 illustrates an exemplary oxygen regulator 400, according to an embodiment of the invention. It is appreciated that the oxygen regulator 400 is an example embodiment of the oxygen regulator 108 of FIG. 1. It is also appreciated that the personal portable oxygen bottle 470 is an example embodiment of the personal portable oxygen bottle 110. As illustrated, the oxygen regulator 400 comprises an inlet port 402 normally connected to a supply of oxygen from the portable personal oxygen bottle 470. The oxygen regulator 400 also comprises a breathing outlet 404 connected to a breathing apparatus of a subject flying in the pressurized aircraft cabin to deliver appropriate flow rate of diluted or undiluted oxygen.

The oxygen regulator 400 is compartmentalized into an oxygen initiation and demand regulation system 406 and a cabin air dilution and delivery system 408. The oxygen initiation and demand regulation system 406 includes an oxygen initiation valve 410 and a cabin air valve 412. The oxygen initiation valve 410 and the cabin air valve 412 are mounted on a shaft 414 coupled to a rotary actuator (e.g., the rotary actuator 218 of FIG. 2) of an electronic control device (e.g., the electronic control device 200 of FIG. 2).

The oxygen initiation and demand regulation system 406 also comprises a balanced oxygen delivery valve 416. The balanced oxygen delivery valve 416 comprises a first chamber 418, a second chamber 420 and a first diaphragm 422. The first chamber 418 is responsive to a bleed pilot pressure of oxygen from the portable personal oxygen bottle 470 received via a port 424. The second chamber 420 is responsive to demand pressure received via a port 426 connected to a demand pressure line 428. The demand pressure line 428 includes a restrictor orifice 430 and is connected to a demand pressure inlet 432 coupled to the breathing outlet 404. The first diaphragm 422 separates the first chamber 418 and the second chamber 420. The first diaphragm 422 is displaced in a direction normal to the first diaphragm 422 in response to differential gas pressure between the first chamber 418 and the second chamber 420.

Further, the balanced oxygen delivery valve 416 comprises a main valve 434, a rod end 436, and a valve stem 438 (e.g., a forwardly extending stem) connecting the main valve 434 and the rod end 436. The main valve 434 comprises a valve member, a valve seat and a light spring, which normally holds the valve member against the valve seat. The main valve 434 also comprises a minimum flow area 434A (e.g., a cut-out in the valve member) and a rearwardly extending stem including a member 434B. As illustrated, the rod end 436 bears against a short leg 442A of a lever 440 (e.g., a bell crank lever) pivoted on a pin 442B. A long leg 442C of the lever 440 bears generally upon a central portion of the diaphragm 422 and rotates about the pin 442B in response to deflection of the diaphragm 422.

According to an embodiment of the present invention, the oxygen initiation and demand regulation system 406 is configured for supplying the appropriate rate of oxygen to the breathing apparatus when pressure data (e.g., the pressure data 210) corresponds to a first altitude (e.g., which falls between a first reference point set by a physician of the subject and a second reference point). The oxygen initiation and demand regulation system 406 is also configured to block flow of dilution air from the pressurized aircraft cabin to the breathing apparatus when the pressure data corresponds to the second reference point.

The cabin air dilution and delivery system 408 includes a cabin air chamber 444 and a mixing chamber 446. The cabin air chamber 444 includes a third chamber 448, a fourth chamber 450 and a second diaphragm 452. The third chamber 448 is configured to receive flow of dilution air from the pressurized aircraft cabin and the fourth chamber 450 is configured to receive the supply of oxygen from the main valve 434.

As illustrated, the second diaphragm 452 separates the third chamber 448 and the fourth chamber 450. The second diaphragm 452 is configured to control mixing ratio by ensuring that pressure of flow of the air in the third chamber 448 and the pressure supply of oxygen in the fourth chamber 450 are substantially equal. The cabin air chamber 444 also includes a cabin air valve 454. The cabin air valve 454 comprises a valve member 454A, a valve seat 454B and a spring 454C which lightly biases the valve member 454A toward the valve seat 454B in response to the position of the second diaphragm 452. Additionally, the cabin air dilution and delivery system 408 includes an emergency dilution shutoff lever 468 coupled to the cabin air valve 454 via a cam 476 and a follower 478. According to an embodiment of the present invention, the cabin air dilution and delivery system 408 is configured for mixing the supply of oxygen with the flow of dilution air from the pressurized aircraft cabin when the pressure data corresponds to the first altitude range (e.g., which falls between the first reference point and the second reference point).

As mentioned above, the oxygen regulator 108 comprises the no flow indicator 126 (as shown in FIG. 1) to indicate a no flow condition when the personal portable oxygen bottle 110 becomes empty or when the oxygen regulator 108 fails. As shown in FIG. 4, a magnet 480 is mounted on the diaphragm 422 and a shaft with magnetic end (not shown) which extends till the setting dial is placed above the magnet 480 with an air gap between them.

When the portable personal oxygen bottle 110 becomes empty and/or fails to supply the pilot flow of oxygen via the bleed line 464, the bleed pilot pressure of oxygen in the first chamber 418 drops below the demand pressure in the second chamber 420. As a result, the diaphragm 422 comes to a neutral position and hence the magnet 480 mounted on the diaphragm 422 moves closer to the shaft. Further, due to repulsion between the shaft magnet and the magnet 480, the shaft experiences an upward movement (e.g., similar to a reed relay switch operation). The upward movement of the shaft causes the red band indicator (marked on other end of the shaft) to pop out which in turn is visible through the hermetic plexiglass window, indicating a no flow condition (e.g., empty condition of the portable personal oxygen bottle 110).

In one example operation of the oxygen regulator 400, at ground level (e.g., at 0 feet), a physician or caretaker of the subject, who is about to fly in the pressurized aircraft cabin, presets a first reference point (e.g., 2000 feet in pressure altitude) using the electronic control device 200 of FIG. 2. At 0 feet pressure altitude, a first inlet port 456 and a first outlet port 458 associated with the oxygen initiation valve 410 and a second inlet port 460 and a second outlet port 462 associated with the cabin air valve 412 are open. Also, the main valve 434 is in closed position and the breathing outlet 404 of the oxygen regulator 400 is connected to the breathing apparatus of the subject flying in the pressurized aircraft cabin.

Also, at ground level, the supply of oxygen to the oxygen regulator 400 is initiated by switching on a quarter turn switching regulator 472. Upon initiation, as the main valve 434 is in the closed position, a minimum flow of oxygen is initiated via the minimum flow area 434A of the main valve 434 to the mixing chamber 446. Also, a pilot flow of oxygen leaks via a bleed line 464 with an orifice 482 to the first chamber 418 through the port 424.

The pilot flow of oxygen received into the first chamber 418 is vented through the first outlet port 458 to a cabin air dilution path and mixed with aircraft cabin air in the third chamber 448. Then, the partially enriched aircraft cabin air is outputted into the mixing chamber 446 through the second outlet port 462. The partially enriched aircraft cabin air and the minimum flow of oxygen received via the minimum flow area 434A are mixed in the mixing chamber 446 and delivered to the breathing apparatus via the breathing outlet 404.

Further, as the aircraft cabin pressure altitude starts increasing (e.g., 0 feet and above), the shaft 414 is actuated based on rotary displacement from the rotary actuator of the electronic control device. The shaft 414 thus drives the oxygen initiation valve 410 and the cabin air valve 412. This causes the oxygen initiation valve 410 to cut off the opening of the first outlet port 458. Further, the oxygen initiation valve 410 closes the first outlet port 458 at 2000 feet (e.g., when the pressure data corresponds to the first reference point), thereby blocking the pilot flow of oxygen to the cabin air dilution path.

Thus, the second outlet port 462 outputs only the aircraft cabin air into the mixing chamber 446 from 2000 feet and above. Closing of the first outlet port 458 at 2000 feet results in gradual increase in the pressure of oxygen in the first chamber 418 compared to the demand pressure in the second chamber 420. This may cause the first diaphragm 422 to deflect downwards. The deflection of the first diaphragm 422 causes the lever 440 to operate the rod end 436 to regulate the main valve 434. In one embodiment, the first diaphragm 422 regulates the main valve 434 to control the supply of oxygen to the breathing apparatus based on an operation of the oxygen initiation valve 410. The opening of the main valve 434 allows the greater amount of oxygen to flow into the mixing chamber 446 via an oxygen line 466. It can be seen in FIG. 4 that, the flow of oxygen is communicated to the mixing chamber 446 via the oxygen line 466 through means such as a jet 474.

In one example embodiment, the first diaphragm 422 may also be deflected due to drop in the demand pressure in the second chamber 420 (e.g., usually when the subject breathes). Thus, the oxygen regulator 400 supplies appropriate rate of pressurized oxygen to the subject based on demand. In other words, if the subject breathes shallow, less amount of oxygen is provided and if the subject breathes heavier, greater amount of oxygen is provided through the main valve opening.

Also, as the aircraft cabin pressure altitude increases above 2000 feet, the shaft 414 further undergoes rotary displacement, thus causing the cabin air valve 412 to gradually reduce the area of opening of the second outlet port 462. As a result, the amount of aircraft cabin air outputted to mixing chamber 446 via the second outlet port 462 is throttled. Finally, the cabin air valve 412 completely closes the second outlet port 462 at 4000 feet (e.g., when the pressure data corresponds to the second reference point), thereby blocking the flow of aircraft cabin air into the mixing chamber 446. Thus, the oxygen regulator 400 supplies approximately about 100% of oxygen to the breathing apparatus via the breathing outlet 404 from 4000 feet and above.

In accordance with the above described operation, the mixing ratio is achieved by virtue of reduction in the area of opening of the cabin air valve 412 such that percentage of oxygen supplied to the breathing apparatus gradually increases with increase in the aircraft cabin pressure altitude and becomes 100% when the pressure data corresponds to the second reference point. It can be noted that, the oxygen regulator 400 can supply approximately about 100% oxygen during emergency (by manual operation of the emergency dilution shutoff lever 468) and upon the aircraft cabin pressure altitude reaching the aircraft cabin decompression point.

In case the aircraft cabin pressure altitude reaching the aircraft cabin decompression point, the oxygen initiation valve 410 and the cabin air dilution valve 412 are closed automatically to stop the flow of aircraft cabin air into the mixing chamber 446 and to instantaneously supply maximum level of oxygen to the breathing apparatus of the subject. Also, the oxygen regulator 400 can supply approximately about 100% oxygen when oxyhaemoglobin saturation data received from the pulse oximeter worn by the subject is lower than the threshold value.

Figure 5:
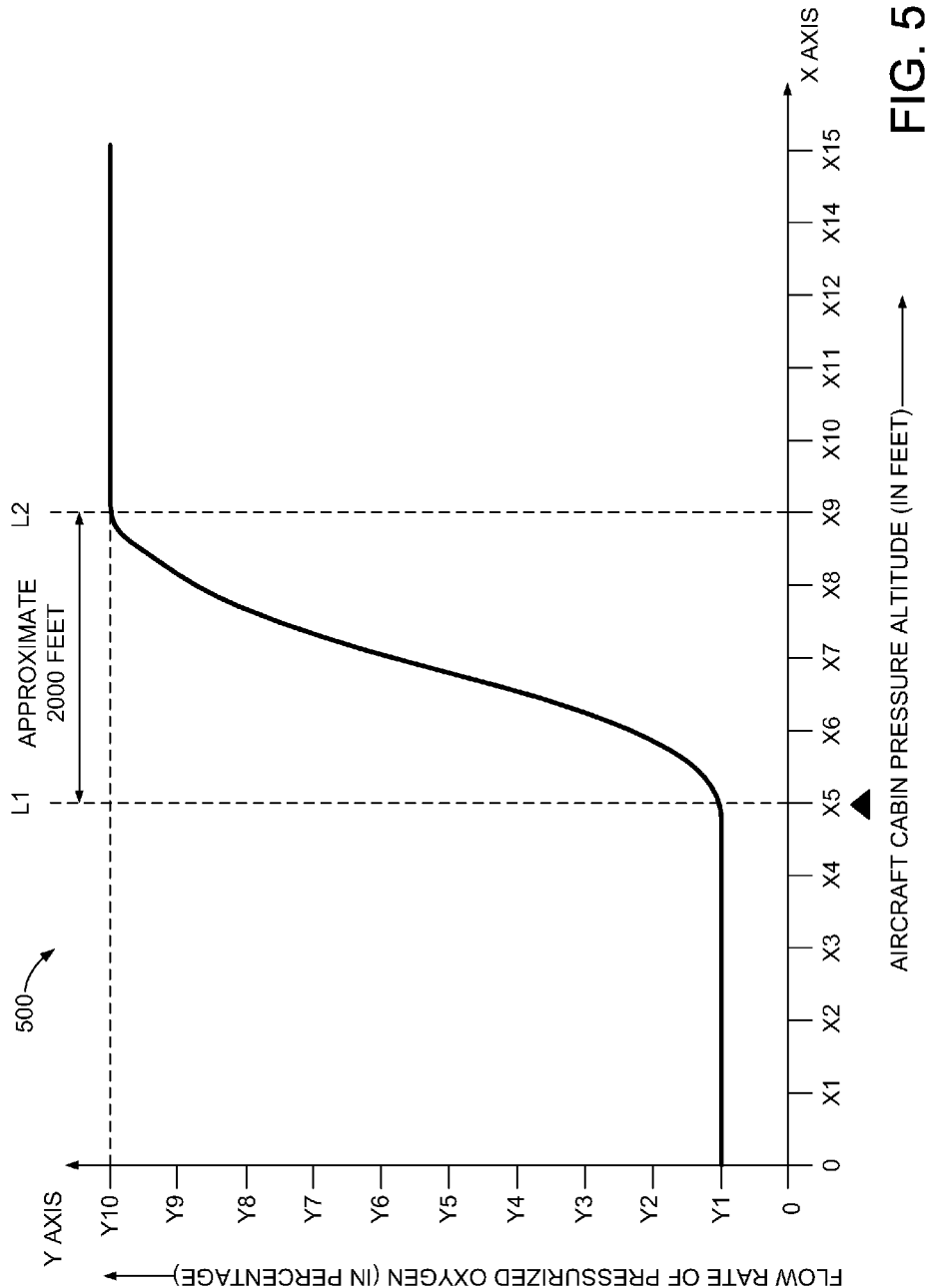
FIG. 5 illustrates an exemplary graph showing flow rate of oxygen delivered from the oxygen regulator of FIG. 4, according to an embodiment of the invention.

FIG. 5 illustrates an exemplary graph 500 showing flow rate of oxygen delivered from the oxygen regulator 400 of FIG. 4, according to an embodiment of the invention. As shown in FIG. 5, X axis represents an aircraft cabin pressure altitude in feet and Y axis represents flow rate of pressurized oxygen delivered to the breathing apparatus in percentage. Further, the graph 500 shows L1 as a first reference point (preset by the physician of the subject) and L2 as a second reference point. The difference between L1 and L2 is approximately 2000 feet.

It can be seen in FIG. 5 that, a small percentage of oxygen (Y1%) is provided to the breathing apparatus at ground level (e.g., 0 feet in pressure altitude) due to the pilot flow of oxygen vented into the cabin air dilution path and minimum flow of pressurized oxygen supplied through the minimum flow area 434A into the mixing chamber 446 to mix with the aircraft cabin air. Further, it can be seen in FIG. 5 that, the small percentage of oxygen (Y1%) is supplied to the breathing apparatus till the aircraft cabin pressure altitude reaches X5 feet.

Furthermore, as depicted in the graph 500, the percentage of flow of pressurized oxygen gradually increases from Y1% to Y10% (e.g., approximately about 100%) as the aircraft cabin pressure altitude increases from X5 feet (at point L1) to X9 feet (at point L2 at which the aircraft cabin air flow into the mixing chamber 446 is stopped and approximately about 100% pressurized oxygen is supplied) and remains constant thereafter. Thus, from the graph 500, it can be construed that the oxygen regulator 400 of FIG. 4 is capable of delivering appropriate flow rate of pressurized oxygen to the breathing apparatus based on the setting provided by the physician of the subject flying in the pressurized aircraft cabin.

Figure 6:
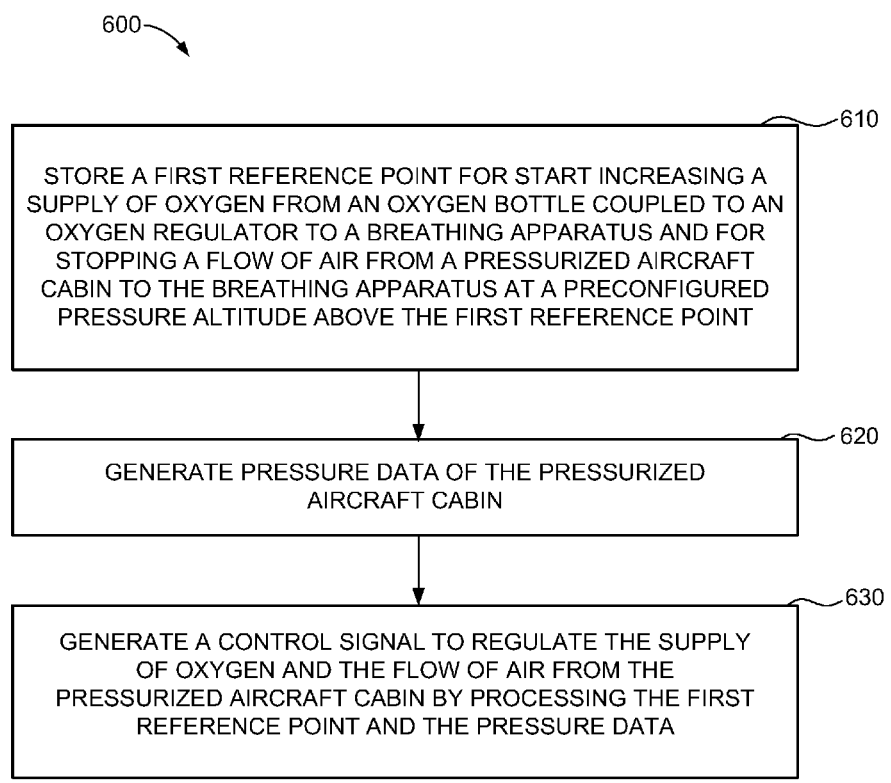
FIG. 6 illustrates a process flowchart of an exemplary method for an electronic control device of an oxygen regulator, according to an embodiment of the invention.

FIG. 6 illustrates a process flowchart 600 of an exemplary method for an electronic control device of an oxygen regulator, according to an embodiment of the invention. In one embodiment, the electronic control device can be used for an oxygen regulator operable inside a pressurized aircraft cabin to supply an appropriate rate of oxygen to a breathing apparatus of a subject in the pressurized aircraft cabin. In operation 610, a first reference point is stored for increasing a supply of oxygen from an oxygen bottle coupled to the oxygen regulator to the breathing apparatus and a second reference point is stored for stopping a flow of dilution air from the pressurized aircraft cabin to the breathing apparatus.

In operation 620, pressure data of the pressurized aircraft cabin is generated using a pressure sensor of the electronic control device. In operation 630, a control signal is generated using a logical control unit coupled to the non-volatile memory and the pressure sensor to regulate the supply of oxygen and the flow of dilution air from the pressurized aircraft cabin via the oxygen regulator to the breathing apparatus by processing the first reference point, the second reference point, and the pressure data. In one example embodiment, the control signal is generated by determining an altitude which corresponds to the pressure data, and setting the control signal based on the altitude.

In various embodiments, the oxygen regulator methods and systems described in FIGS. 1 through 6 enable subjects with impaired/reduced pulmonary function who would be otherwise unable, to travel safely in a pressurized aircraft cabin (with the attendant lower oxygen levels and lower ambient pressure (e.g., higher altitude of 5000-7000 feet) than is normally encountered at ground level) safely without risk of respiratory distress (hypoxia, hyperventilation, syncope, and the like). In other words, the above-described oxygen regulator system provides the subject a higher partial pressure of oxygen ($PO_2$) in lung alveoli and hence an equivalent lower altitude to ensure sufficient saturation of hemoglobin as compared to other passengers in the same pressurized aircraft cabin who are breathing aircraft cabin air. Thus, the above-described oxygen regulator system enables safe, economic, unhindered passage/evacuation of the subject with impaired/reduced pulmonary function.

The above-described oxygen regulator system is adaptable/configurable and suitable for use by individuals based on tests (e.g., lung forced expiration volume (FEV) test, lung capacity test, etc.) and is targeted for use by a small percentage of population. The above-described oxygen regulator system facilitates the subject to travel longer distances using a portable personal oxygen bottle (e.g., 2 to 7 liters capacity) as oxygen is not wasted and is supplied as per the requirement. In one embodiment, the oxygen regulator system automatically delivers appropriate flow rate of diluted or undiluted oxygen without intervention by a physician/medical attendants of the invalid subject once the initial setting has been determined as suiting the invalid person.

Further, the above-described oxygen regulator system delivers approximately about 100% pressurized oxygen during emergency and when aircraft cabin pressure altitude reaches an aircraft cabin decompression point so that the subject can stay on a single supply (independent) without the need to switch over to a aircraft cabin drop down/pull down mask.

A skilled person will recognize that many suitable designs of the systems and processes may be substituted for or used in addition to the configurations described above. It should be understood that the implementation of other variations and modifications of the embodiments of the invention and its various aspects will be apparent to one ordinarily skilled in the art, and that the invention is not limited by the exemplary embodiments described herein and in the claims. Therefore, it is contemplated to cover the present embodiments of the invention and any and all modifications, variations, or equivalents that fall within the true spirit and scope of the basic underlying principles disclosed and claimed herein.

What is claimed is:

1. An electronic control device for an oxygen regulator operable inside a pressurized aircraft cabin to supply an appropriate rate of oxygen to a breathing apparatus of a subject in the pressurized aircraft cabin, comprising:
   a non-volatile memory configured for storing a first reference point to start gradually increasing a supply of oxygen from an oxygen bottle coupled to the oxygen regulator to the breathing apparatus and to gradually stop a flow of dilution air from the pressurized aircraft cabin to the breathing apparatus with increasing aircraft cabin pressure altitude above the first reference point;
   a pressure sensor configured for generating pressure data of the pressurized aircraft cabin; and
   a logical control unit coupled to the non-volatile memory and the pressure sensor and configured for generating a control signal to regulate the supply of oxygen from the oxygen bottle and the flow of dilution air from the pressurized aircraft cabin via the oxygen regulator to the breathing apparatus by processing the first reference point and the pressure data, wherein the oxygen regulator outputs approximately about 100% pressurized oxygen into the breathing apparatus upon reaching a preconfigured pressure altitude above the first reference point.

2. The device of claim 1, wherein the non-volatile memory comprises a flash memory.

3. The device of claim 1, further comprising a serial port coupled to the logical control unit for receiving oxyhaemoglobin saturation data forwarded by a pulse oximeter worn by the subject.

4. The device of claim 3, wherein the oxygen regulator is configured to increase the supply of oxygen to a maximum level when the oxyhaemoglobin saturation data is less than a threshold value.

5. The device of claim 1, wherein the non-volatile memory is configured to store a first lookup table used to convert the pressure data to a corresponding altitude and a second lookup table used to convert the corresponding altitude to a rotary displacement.

6. The device of claim 5, wherein the logical control unit comprises a first comparator module for determining the corresponding altitude using the first lookup table and a second comparator module for generating the control signal based on the rotary displacement.

7. The device of claim 6, further comprising an amplifier coupled to the logical control unit for amplifying the control signal.

8. The device of claim 7, further comprising a rotary actuator coupled to the amplifier for performing the rotary displacement based on the control signal.

9. The device of claim 8, wherein the oxygen regulator comprises:
an oxygen initiation and demand regulation system configured for supplying the appropriate rate of oxygen to the breathing apparatus when the pressure data corresponds to a first altitude which falls between the first reference point and the preconfigured pressure altitude and for blocking the flow of dilution air from the pressurized aircraft cabin to the breathing apparatus when the pressure data corresponds to the preconfigured pressure altitude above the first reference point; and
a cabin air dilution and delivery system coupled to the oxygen initiation and demand regulation system and configured for mixing the supply of oxygen with the flow of dilution air from the pressurized aircraft cabin when the pressure data corresponds to the first altitude which falls between the first reference point and the preconfigured pressure altitude above the first reference point.

10. The device of claim 9, wherein the oxygen initiation and demand regulation system comprises:
an oxygen initiation valve configured to close when the pressure data corresponds to the first reference point;
a cabin air valve configured to close when the pressure data corresponds to the preconfigured pressure altitude above the first reference point; and
a balanced oxygen delivery valve, comprising:
a first chamber;
a main valve;
a second chamber; and
a second diaphragm for separating the first chamber and the second chamber and for regulating the main valve to control the supply of oxygen to the breathing apparatus based on an regulating operation of the oxygen initiation valve.

11. The device of claim 10, further comprising a shaft driving the oxygen initiation valve and the cabin air valve coupled to the rotary actuator.

12. The device of claim 11, wherein the shaft is actuated based on the rotary displacement.

13. The device of claim 10, wherein the cabin air dilution and delivery system comprises:
a mixing chamber; and
a cabin air chamber, comprising
a third chamber;
a fourth chamber; and
a second diaphragm for separating the third chamber and the fourth chamber, wherein the third chamber is configured to receive the flow of dilution air from the pressurized aircraft cabin and the fourth chamber is configured to receive the supply of oxygen from the main valve.

14. An oxygen regulator system operable inside a pressurized aircraft cabin to supply an appropriate rate of oxygen to a breathing apparatus of a subject in the pressurized aircraft cabin, comprising:
an electronic control unit, comprising:
a non-volatile memory configured for storing a first reference point to start gradually increasing a supply of oxygen from an oxygen bottle coupled to an oxygen regulator to the breathing apparatus and to gradually stop a flow of dilution air from the pressurized aircraft cabin to the breathing apparatus with increasing aircraft cabin pressure altitude above the first reference point;
a pressure sensor configured for generating pressure data of the pressurized aircraft cabin;
a logical control unit coupled to the non-volatile memory and the pressure sensor and configured for generating a control signal to regulate the supply of oxygen from the oxygen bottle and the flow of dilution air from the pressurized aircraft cabin via the oxygen regulator to the breathing apparatus by processing the first reference point and the pressure data, wherein the oxygen regulator outputs approximately about 100% pressurized oxygen into the breathing apparatus upon reaching a preconfigured pressure altitude above the first reference point; and
a rotary actuator coupled to the logical control unit for generating a rotary displacement based on the control signal; and
the oxygen regulator coupled to the electronic control unit and configured to control the supply of oxygen and the flow of dilution air from the pressurized aircraft cabin based on the control signal.

15. The system of claim 14, further comprising a pulse oximeter worn by the subject and coupled to the electronic control unit.

16. The system of claim 14, wherein the electronic control unit further comprises a front panel which includes a set button for entering the first reference point; a display for displaying a set altitude or a pulse and breathing rate; and a no flow indicator.

17. The system of claim 14, wherein the oxygen regulator further comprises a quarter turn switching regulator to initiate the supply of oxygen from the oxygen bottle.

18. The system of claim 14, wherein the oxygen regulator further comprises an emergency dilution shutoff lever operable for the supply of oxygen at a maximum level.

19. A method of an electronic control device for an oxygen regulator operable inside a pressurized aircraft cabin to supply an appropriate rate of oxygen to a breathing apparatus of a subject in the pressurized aircraft cabin, comprising:

storing a first reference point for gradually increasing a supply of oxygen from an oxygen bottle coupled to the oxygen regulator to the breathing apparatus and for gradually stopping a flow of dilution air from the pressurized aircraft cabin to the breathing apparatus with increasing aircraft cabin pressure altitude above the first reference point;

generating pressure data of the pressurized aircraft cabin using a pressure sensor of the electronic control device; and generating a control signal using a logical control unit coupled to the non-volatile memory and the pressure sensor to regulate the supply of oxygen and the flow of dilution air from the pressurized aircraft cabin via the oxygen regulator to the breathing apparatus by processing the first reference point and the pressure data, wherein the oxygen regulator outputs approximately about 100% pressurized oxygen into the breathing apparatus upon reaching a preconfigured pressure altitude above the first reference point.

20. The method of claim 19, wherein the generating the control signal comprises:

determining an altitude which corresponds to the pressure data; and setting the control signal based on the altitude.

* * * * *